(12) United States Patent
Ernst et al.

(10) Patent No.: US 6,632,389 B1
(45) Date of Patent: Oct. 14, 2003

(54) UNDERWATER OR UNDER-HYDROCARBON PELLETIZING OF BIOLOGICALLY-ACTIVE-COMPOUND-CONTAINING MELTS

(75) Inventors: Andreas Ernst, Worms (DE); Thomas Kessler, Schifferstadt (DE); Gunther Berndl, Herxheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 265 days.

(21) Appl. No.: 09/643,725

(22) Filed: Aug. 23, 2000

(30) Foreign Application Priority Data

Sep. 10, 1999 (DE) .......................................... 199 43 501

(51) Int. Cl.$^7$ ............................................... B29C 47/00
(52) U.S. Cl. ..................... 264/141; 264/178 R; 424/465
(58) Field of Search .................................. 364/140, 141, 364/142, 143, 144, 5, 13, 14, 178 R, 179, 180, 182, 203; 424/465

(56) References Cited

U.S. PATENT DOCUMENTS

| 4,150,595 | A |   | 4/1979  | Loffler et al. .................. 83/171 |
| 4,264,553 | A |   | 4/1981  | Loo ........................... 264/142 |
| 4,801,460 | A |   | 1/1989  | Goertz et al. ................. 424/465 |
| 4,880,585 | A |   | 11/1989 | Klimesch et al. ............. 264/141 |
| 5,143,673 | A |   | 9/1992  | Grimminger ................. 264/142 |
| 6,120,802 | A | * | 9/2000  | Breitenbach et al. ........ 424/464 |
| 6,335,033 | B2 | * | 1/2002 | Oshlack et al. .............. 424/451 |

FOREIGN PATENT DOCUMENTS

| DE | 26 46 309   | 4/1979  |
| DE | 195 36 387  | 4/1997  |
| DE | 198 09 242  | 9/1999  |
| EP | 0 240 904   | 10/1987 |
| EP | 0 240 906   | 10/1987 |
| JP | 07 047 545  | 2/1995  |

* cited by examiner

*Primary Examiner*—Mark Eashoo
*Assistant Examiner*—Geoffrey P. Shipsides
(74) *Attorney, Agent, or Firm*—Keil & Weinkauf

(57) ABSTRACT

A process for producing pellets comprising biologically active substances in which the biologically active substances are homogeneously dispersed in a matrix based on at least one thermoplastic polymer, which polymer has in aqueous medium a pH-dependent solubility, by homogeneous mixing of the starting materials in the melt and subsequent extrusion and shaping, which comprises the shaping being performed in a cooling medium in which the pellets are not soluble or dispersible.

9 Claims, No Drawings

UNDERWATER OR UNDER-HYDROCARBON PELLETIZING OF BIOLOGICALLY-ACTIVE-COMPOUND-CONTAINING MELTS

The present invention relates to a process for producing pellets which comprise active compounds and are based on thermoplastic polymers by melt extrusion and underwater pelletizing and also relates to corresponding pellets and their use.

Underwater pelletizing is generally known as an effective pelletizing method for thermoplastic materials for the industrial production of plastic pellets.

Corresponding apparatuses and processes are described, for example, in DE-A 2646309, U.S. Pat. No. 4,264,553 or U.S. Pat. No. 5,143,673. In these the hot plastic melt is transported from an extruder via a perforated disk directly into a liquid cooling medium, in this case water. The exiting plastic strands are divided into pellets by a cutting apparatus mounted at the perforated disk and are transported away by the generally recirculated water, separated off and dried. By means of this liquid-cooled process it is possible to produce very small particle sizes uniformly, continuously and on an industrial scale down to the submillimeter range. By using cooling media having a high heat capacity and a high heat transfer, such as water, the still-plastic pellets are rapidly cooled, do not stick together and may be produced in very uniform shape and size.

In comparison, using die-face cutting with air cooling for pelletizing the extruded strands is considerably more difficult because of the slow and poor heat transfer.

Formulations which contain active compounds, for example comprising vitamins as active compound, are administered, to maintain the health of humans and animals, in parallel to food intake or are added to the diet as additive. A large proportion of the formulations of vitamins, vitaminoids or other food supplements manufactured is required for animal nutrition. Since the feedstuffs used there are supplied as ground material having a mean particle size of 0.3–0.5 mm, added feed additives—to prevent separation—should have roughly the same size and uniformity. Uniform particle size is also of particular importance for producing pellets for drugs, since the dissolution behavior and thus the bioavailability are dependent on the particle size. The previously used drug pellets, feed supplements or feed additives are therefore usually produced in complex and expensive grinding, pelletizing and spraying processes.

Preparations which contain active compounds and are produced by melt extrusion are generally known. Extrusion of melts of water-soluble polymers, which melts contain active compounds, preferably copolymers of vinylpyrrolidone, is disclosed, for example, by EP-A 240904 and EP-A 240906. EP-A 240 906 also describes the melt extrusion of active-compound-containing mixtures, copolymers of methyl methacrylate and acrylic acid, copolymers of vinyl acetate and crotonic acid, and also ethylene/vinyl acetate copolymers. They are shaped via injection molding or extrusion with subsequent shaping of the still-plastic strand, for example by die-face cutting to form pellets or shaping to form tablets. In all said examples shaping is performed in air. The pharmaceutical forms thus produced are generally water-soluble.

Thus, for example, DE-A 19536387 also describes melt extrusion and shaping of vitamin-containing products. Water-soluble, thermoplastic hydroxypropylcelluloses are used as matrix. In the examples, inter alia, melts of vitamin C or β-carotene together with hydroxypropylcellulose are pressed by shaping calenders to form tablets. In addition, die-face cutting of the water-soluble matrix to form pellets is mentioned.

Although such water-soluble formulations can be produced using melt extrusion and subsequent pelletizing in air, it is a disadvantage that frequently, owing to the poor heat transfer, the required (small) particle size, uniformity and large-scale feasibility cannot be achieved in this manner.

It is an object of the present invention to develop an inexpensive and simple production process for formulations which contain active compounds, for example drugs or feed additives, which dissolve or disperse on their own in water or in the gastrointestinal tract.

We have found that this object is achieved, surprisingly, if mixtures which comprise active compounds are melt-extruded with polymers which are water-insoluble in a certain pH range and are water-soluble in another pH range.

Accordingly, a process was found for producing pellets which comprise biologically active substances in which the biologically active substances are homogeneously dispersed in a matrix based on at least one thermoplastic polymer, which polymer has in aqueous medium a pH-dependent solubility, by homogeneous mixing of the starting materials in the melt and subsequent extrusion and shaping, which comprises the shaping being performed in a cooling medium in which the pellets are not soluble or dispersible.

To carry out the process of the invention, the starting materials are mixed to form a homogeneous melt. This can be done, for example, by introducing a physical premix of solid starting materials into a suitable extruder or kneader, melting the mixture with the use of mechanical and thermal energy, and transporting the hot, still-plastic melt through a perforated disk or a nozzle plate directly into a liquid cooling medium. If the formulation also comprises liquid constituents, it is advisable to add these separately via a metering pump. If thermally labile active compounds are used, it can also be advisable firstly to prepare a melt of the thermoplastic polymers and, if desired, other formulation aids, and only then to add the active compound. The melting is preferably performed in a screw machine, in particular in a double-screw extruder, which is preferably corotating. The process of the invention is preferably carried out in the absence of solvents. In the event that it should be necessary to add to the mixture one or more of the starting materials in the form of a solution, the solvents used here can be removed in the downstream extruder zones by applying a vacuum. The extruded, still-thermoplastic mass then no longer contains solvent.

The starting materials can be melted, depending on composition of the mixture, at from 50 to 300° C., preferably from 70 to 250° C.

The exiting plastic strands are divided into pellets by a cutting apparatus mounted at the perforated disk or nozzle plate, and are transported away by the preferably recirculated cooling medium, separated off and dried. Suitable cooling media are, for example, liquid hydrocarbons such as paraffins or aromatic hydrocarbons, or preferably water. If water is used as cooling medium, according to the invention the pH of the water is set using acids or bases such that the matrix comprising the active compounds does not dissolve or disperse itself therein. According to the invention this is intended to mean that no more than 1 g/l of the pellets may be dissolved or dispersed in water.

By using cooling media having a high heat capacity and a high heat transfer, such as water, the still-plastic pellets are rapidly cooled, do not stick together and may be produced in very uniform shape and size. Preference is given to pellets produced having mean particle sizes of from 0.1 to 5, preferably from 0.3 to 3, mm.

The process of the invention is suitable in principle for producing pellets comprising biologically active substances in which one or more biologically active substances is/are homogeneously dispersed in a matrix based on thermoplastic polymers. Homogeneously dispersed can also mean according to the invention that the biologically active substances are present molecularly dispersed in the matrix, that is are what are termed "solid solutions".

Biologically active substances which can be used are generally all substances which are to be released in the gastrointestinal tract of humans and animals. These can be, for example, active drug compounds, vitamins, vitaminoids, carotenoids, enzymes, hormones, amino acids or "nutraceuticals", that is to say food supplements and dietetic compositions.

In addition, it is also possible to formulate active plant protection compounds, laundry detergent constituents, odorants and flavorings or other active substances in the above-described manner.

The process of the invention and the apparatus of the invention are suitable for preparing particulate preparations of biological substances. Biologically active substances are according to the invention substances which cause a biological effect in living organisms.

The process of the invention is suitable, for example, for formulating the following substances or their physiologically acceptable salts, in which case the salts can also be produced in situ in the extruder:

Antiinfective Compositions

Aciclovir, aminoglycosides, amphotericin B, azole-antimycotics, clotrimazole, itraconazole, sepraconazole, clindamycin, cephalosporins, chloramphenicol, erythromycin, 5-fluorouracil, etoposide, flucytosine, ganciclovir, griseofulvin, gyrase inhibitors, isoniazid, lincosamides, mebendazole, mefloquine, metronidazole, nitroimidazoles, novobiocin, platinum compounds, polymyxin B, praziquantel, pyrimethamine, rifampicin, saquinavir, streptomycin, sulfonamides, tetracyclines, trimethoprim, vancomycin, zidovudine;

Antipyretics, analgesics, antiinflammatories, paracetamol, ibuprofen, ketoprofen, oxaprozin, acetylsalicylic acid, morphine, oxaprozin, propoxyphene, phenylbutazone;

Antibiotics

Rifampicin, griseofulvin, chloramphenicol, cycloserine, erythromycin, penicillins, such as penicillin G, streptomycin, tetracycline;

Antiepileptics

Hydantoins, carbamazepine;

Antitussives und Antiasthmatics

Diphenhydramine;

Antirheumatics

Chloroquine, indomethacin, gold compounds, phenylbutazone, oxyphenylbutazone, penicillamine;

Hypnotics

Barbiturates, phenobarbital, zolpidem, dioxopiperidines, ureides;

Insecticides

Aldrin, dieldrin, chlorphenotan, hexachlorocyclohexane;

Herbicides

Vinclozolin, strobilurines;

Antipsychotics, Neuroleptics

Perazine, promazine, sulpiride, thioridazine, chlorpromazine, meprobamate, triflupromazine, melperone, clozapine, risperidone, reserpin;

Tranquillizers;

Antidepressives

Imipramine, paroxetine, viloxazine, moclobemide;

Psychotonics;

Psychomimetics;

Diuretics

Potassium canrenoate, loop diuretics, furosemide, hydrochlorothiazide, spironolactone, thiazides, triamterene;

Hormones

Androgens, antiandrogens, gestagens, glucocorticoids, oestrogens, cortisol, dexamethasone, prednisolone, testosterone, Adiuretin, oxytocin, somatropin, insulin;

Immunosuppressants

Cyclosporin;

Bronchodilators;

Muscle Relaxants, Tranquillizers

Carisoprodol, tetrazepam, diazepam, chlordiazepoxide;

Enzymes

Lipase, phytase;

Antigouts

Allopurinol, colchicine;

Anticoagulants

Coumarins;

Antiepileptics

Phenytoin, phenobarbital, primidone, valproic acid, carbamazepine;

Antihistamines

Chlorphenoxamine, dimenhydrinate;

Antiemetics;

Antihypertensives, Antiarrhythmics

Lidocaine, procainamide, quinidine, calcium antagonists, glycerol trinitrate, isosorbide dinitrate, isosorbide 5-mononitrate, pentaerythrityl tetranitrate, nifedipine, diltiazem, felodipine, verapamil, reserpine, minoxidil, reserpiline, captopril, enalapril, lisinopril;

Sympathomimetics

Norfenefrine, oxedrine, midodrine, phenylephrine, isoprenaline, salbutamol, clenbuterol, ephedrine, tyramine, β-blockers such as alprenolol, metoprolol, bisoprolol;

Antidiabetics

Biguanides, sulfonylureas, carbutamide, tolbutamide, glibenclamide, metformin, acarbose, troglitazone;

Iron preparations;

Vitamins and Vitaminoids

For example ascorbic acid, tocopherol, tocopherol acetate, vitamin A and vitamin A derivatives, vitamin K and vitamin K derivatives or vitamin D and vitamin D derivatives, riboflavin, vitamin $B_{12}$, nicotinic acid, nicotinamide, pyridoxin hydrochloride, biotin, folic acid, folic acid derivatives, such as tetrahydrofolic acid, 5-methyltetrahydrofolic acid, 10-formyltetrahydrofolic acid or 5-formyltetrahydrofolic acid;

carotenoids, for example β-carotene, lycopene, lutein, astaxanthin or zeaxanthin;

polyunsaturated fatty acids, for example linoleic acid, linolenic acid, arachidonic acid, docosahexaenoic acid or eicosapentaenoic acid;

compounds having vitamin character or coenzyme character, for example carnitine, choline chloride, taurine, creatine, ubiquinones, S-methylmethionine or S-adenosylmethionine;

ACE Inhibitors
   Captopril, ramipril, enalapril;
   Anabolics;
   Iodine compounds;
   X-ray contrast materials;
   Compounds having CNS activity;
Antiparkinsonians
   Biperiden, benzatropine, amantadine, opioid analgesics, barbiturates, benzodiazepines, disulfiram, lithium salts, theophylline, valproinate, neuroleptics;
   Cytostatics;
   Antispasmolytics;
Vasodilators
   Naftidrofuryl, pentoxifylline.

Preparations of the biologically active substances can also be obtained in the form of "solid solutions". The term "solid solutions" is familiar to those skilled in the art (see Chiou and Riegelman, J. Pharm. Sci. 60, 1281–1302 (1971)). In solid solutions of active pharmaceutical compounds in polymers or other matrices, the active compound is present in the matrix in molecularly dispersed form.

Suitable matrix components are in principle all thermoplastic polymers which have a pH-dependent water solubility. In particular, these are polymers having acid (e.g. carboxylate) or base (e.g. amine) functionalities or having acid- or base-unstable functionalities (e.g. esters).

Polymers which can be used are, for example, the homopolymers and copolymers of N-vinylpyrrolidone, vinyl acetate being a preferred comonomer.

Suitable polymers are, for example, also copolymers of vinyl acetate and crotonic acid, for example Luviset® CA 66, BASF, a copolymer of 90% by weight of vinyl acetate and 10% by weight of crotonic acid. Similarly suitable are copolymers of methacrylic acid and ethyl acrylate, for example Kollicoat® MAE 100 P, BASF, or Luvimer® 100 P (terpolymer of 67% by weight of t-butyl acrylate, 23% by weight of methacrylic acid and 10% by weight of ethyl acrylate, and in addition non-hydrolyzed or partially hydrolyzed polyvinyl acetates, for example the Vinnapas brands (up to 100% vinyl acetate) from Wacker, and, for example, dimethylaminoethyl acrylate copolymers.

Preferably, polymers are used which contain, as comonomers, monoolefinically unsaturated carboxylic acids which can be polymerized in a free-radical manner, for example acrylic acid, methacrylic acid or crotonic acid.

Additional comonomers which are preferably used are monoolefinically unsaturated carboxylic esters having up to 6 carbon atoms, for example methyl, ethyl, n-butyl or tert-butyl methacrylate, methyl, ethyl, n-butyl or tert-butyl acrylate, vinyl acetate and vinyl propionate.

Particular preference is given to polymers which contain at least 30% by weight of acrylic acid or methacrylic acid as comonomer. In addition, terpolymers containing, for example, dimethylaminoethyl acrylate and derivatives, butyl esters or acrylamides can also be used.

Particular preference is given to matrices comprising biologically active substances and polymers, which matrices, if desired, additionally comprise plasticizers and other formulation aids, and dissolve or disperse in water or aqueous systems at a pH of >5, so that a solid dosage form of the respective formulation sufficiently rapidly and completely releases the active substance into the gastrointestinal tract of animals or humans. At pHs of <3, these formulations should not be soluble or dispersible, or should be significantly more poorly soluble or dispersible, in water or aqueous systems. This is the case, for example, with the use of hydrophobic active substances such as vitamin A with matrix polymers of acrylic acid or methacrylic acid and acrylic esters (methacrylic and acrylic esters) having an acrylic acid or methacrylic acid content of ≧30%. However, the release rate depends in each case on the polymer matrix used, the plasticizers optionally used and on other additives, and also on the active substance.

In addition to polymer and active compound, formulations of this type can comprise customary additives relating to extrusion and formulation, for example plasticizers and stabilizers.

Plasticizers which are used are, for example, polyethylene glycols, triacetin, triethyl citrate or propanediol.

Stabilizers, Surfactants etc. and Extrusion Aids

Depending on field of application and processability, the contents of active compound, polymer and additives can vary within broad ranges. The sole boundary conditions are the thermoplastic processability and the described solubility properties of the formulation. Generally, the active compound content will be in a range from 5 to 90, preferably from 5 to 80, particularly preferably from 5 to 60% by weight. The remainder is formed by polymers, generally from 10 to 55% by weight, and formulation aids.

Using the process of the invention it is possible to produce active-compound-containing formulations by melt extrusion and underwater pelletizing in an insoluble pH range and, after separation, to redissolve these in a soluble pH range (underwater pelletizing of active-compound-containing melts having pH-dependent solubility). Manufacture using water as cooling medium is inexpensive, environmentally compatible, safe and simple, but, for reasons of product solubility, it can be necessary to use other liquid media, for example mineral oils, vegetable oils or other organic solvents. In addition, it is possible to add to the water soluble additives, for example salts, in order to decrease the solubility of the formulation. Under the abovementioned conditions, with the choice of matrices, recourse no longer has to be made to pH-dependent solubilities. For example, it is conceivable to pelletize an active-compound-containing matrix of the water-soluble nonionic polymer polyvinylpyrrolidone or cellulose derivatives or VP copolymers in a hydrocarbon as cooling medium. Polyvinylpyrrolidine is virtually insoluble in paraffins. These products could then re-release the active substance in water.

Thus, it is for example possible to pelletize a polymeric thermoplastic matrix of methacrylic acid and ethyl acrylate at pHs of 3–4 under water and, after the separation, to dissolve the resultant pellets in water at pHs of 7–8. The dissolution properties of the overall formula are codetermined by the active compounds, plasticizers and additives used.

The pellets of the invention are suitable in particular for use in feedstuffs, food supplements or dietetic compositions, and in addition for producing drugs for the human and veterinary sector and for plant protection compositions.

The pellets are also suitable for laundry detergent formulations which comprise enzymes or aroma substances as biologically active substances.

The pellets can be used as such. In addition, they are suitable as capsule fillings or for pressing to form tablets.

EXAMPLES

General Preparation Protocol

All solid starting materials are mixed in accordance with the formula and are introduced via a differential metering balance into the transport zone of a corotating closely intermeshing double-screw extruder ZSK 30 (Werner & Pfleiderer GmbH, Stuttgart, Germany) at room temperature. After a further transport zone (80° C.), there follow 2 heating zones (110° C.) and then 4 mixing and kneading zones (120° C.) onto which is mounted a lateral pump unit via which the appropriate liquid components are fed in. After two further zones (120° C.), the homogenized melt is fed via a gear pump (140° C.) into an underwater pelletizing unit of the Gala laboratory pelletizing type: Lab Pelletizing System LPS (9—approximately 50 kg/h) (GALA Kunststoff-Kautschukmaschinen GmbH, Xanten, Germany). Via the start-up valve, the melt (140° C.) is run via a pelletizing die 30×1.0 mm having a rotary knife into a closed process water circuit (25° C.), where the pH of the process water is set to pH 3 using one molar sulfuric acid. The pellets thus produced are separated from the process water via a circulation pump in a centrifugal dryer. The process water is set in advance to the appropriate pH using acids or bases depending on the matrix used.

Example 1

Solid Starting Materials

Kollicoat MAE 100 P (methacrylic acid/ethyl acrylate copolymer, 50% by weight of MAA, 50% by weight of EA; BASF AG), powder Lutrol E 6000 (polyethylene glycol, MW 6000 BASF AG), powder Liquid Component Vitamin A oil: mixture of vitamin A acetate, 2.8 million IU/G unstab. (80% by weight) (BASF AG) and ethoxyquin (20% by weight) (Raluquin®, Raschig AG) was fed at 60° C. via a heated pump unit.

A physical mixture of 65 parts by weight of Kollicoat MAE 100 P and 15 parts by weight of Lutrol E 6000 was, as described in the general procedure, metered into the extruder, transported, homogenized and melted. Via a lateral metering zone, 20 parts by weight of vitamin A oil were run in and incorporated. The melt was then, in a manner described above, processed to form spherical 1 mm pellets by underwater pelletizing.

Dispersion 1.0 g of the pellets prepared by underwater pelletizing was charged, with stirring (magnetic stirrer Ikamag RET-G, Janke & Kunkel GmbH & Co. KG., Staufen, Germany; Teflon stirrer 1=4 cm) into a cylindrical 1 l glass vessel having a diameter of 10 cm containing 1000 ml of distilled water (T=20° C.) at a stirrer speed of 300 rpm (0.1% strength dispersion). The distilled water, in a first case, had been previously set to pH 3 (sample 1) using 0.1 M HCl and, in a second case, to pH 8 (sample 2) using 0.1 M NaOH. After 20 minutes, the dispersion was filtered off through a 50 μm screen and the screen residue was determined after drying (vacuum drying oven, 40° C., 4 h) in % by weight, based on the starting amount (1.0 g).

| Example 1 | Screen residue [% by weight] |
| --- | --- |
| Sample 1 | 98 |
| Sample 2 | 0.3 |

The prepared formula from Example 1 could be pelletized under water at pH 3 without loss of mass. It dispersed virtually completely in the course of 20 min in water having a pH of 8, which would enable intestinal absorption.

Example 2

Solid Starting Materials

Luvimer 100 P (t-butyl acrylate/methacrylic acid/ethyl acrylate terpolymer), BASF AG Liquid Component Vitamin A oil: mixture of vitamin A acetate, 2.8 million IU/G unstab. (80% by weight) (BASF AG) and ethoxyquin (20% by weight) (Raluquin, Raschig AG) were run in at 60° C. via a heated pump unit.

80 parts by weight of Luvimer 100 P were, as described in the general procedure, metered into the extruder, transported and melted. Via a lateral metering zone, 20 parts by weight of vitamin A oil were run in and incorporated. The melt was then, in the above-described manner, processed by underwater pelletizing to form spherical, beige, slightly cloudy but homogeneous pellets having a diameter of 1 mm.

Example 3

Solid Starting Materials

Ascorbic acid, vitamin C (crystalline product), BASF AG

Luviset CA 66 (crotonic acid/vinyl acetate copolymer), BASF AG

Liquid Component

Triacetin (triacetylpropanetriol), Fluka Chemie AG, Switzerland

A physical mixture of 60 parts by weight of Luviset CA 66 and 30 parts by weight of vitamin C was, as described in the general procedure, metered into the extruder, homogenized and transported. 10 parts of triacetin were run in via a lateral metering zone and incorporated. The melt was then processed, in a manner described above, by underwater pelletizing to give spherical 1 mm pellets.

The resultant pellets (1 g per liter of water) were completely soluble in water at pH 8 in the course of 2 hours. Pure Luviset CA 66 polymer beads dissolved significantly slower under these conditions (>8 hours).

Example 4

A physical mixture of 69 parts by weight of Kollicoat MAE 100 P, 30 parts by weight of ibuprofen and 1 part by weight of highly disperse silicic acid (Aerosil 200) was, as described in the general protocol, metered into the extruder, transported, homogenized and melted. The melt was then processed by underwater pelletizing to give spherical pellets having a mean diameter of 1 mm.

We claim:

1. A process for producing pellets comprising biologically active substances in which the biologically active substances are homogeneously dispersed in a matrix based on at least one thermoplastic polymer, which polymer has in aqueous medium a pH-dependent solubility, so that in one pH range it is water insoluble and in a different pH range it is water soluble, by homogeneous mixing of the starting materials in the melt and subsequent extrusion and shaping, which comprises the shaping being performed in a cooling medium, which cooling medium is a liquid hydrocarbon or water containing an acid or base such that the pH is such that the pellets do not dissolve or are not dispersible.

2. A process as claimed in claim 1, wherein the cooling medium used is water containing an acid or base such that the pH is such that the pellets do not dissolve or are not dispersible.

3. A process as claimed in claim 1, wherein the thermoplastic polymers contain acidic or basic groups or groups which are unstable in acids or bases.

4. A process as claimed in claim 1, wherein polymers are used which contain monoolefinically unsaturated carboxylic acids as comonomer.

5. A process as claimed in claim 1, wherein the polymers contain one or more comonomers selected from the group consisting of acrylic acid, methacrylic acid and crotonic acid.

6. A process as claimed in claim 1, wherein the polymers contain monoolefinically unsaturated carboxylic esters as comonomers.

7. A process as claimed in claim 1, wherein the polymers contain one or more comonomers selected from the group consisting of methyl acrylate, ethyl acrylate, butyl acrylate, methyl methacrylate, ethyl methacrylate, butyl methacrylate, vinyl acetate and vinyl propionate.

8. A process as claimed in claim 1, wherein the polymers contain at least 30% by weight of acrylic acid or methacrylic acid as comonomer.

9. A process as claimed in claim 1, wherein formulation aids are additionally incorporated.

* * * * *